United States Patent [19]

Klingner

[11] Patent Number: 5,140,986
[45] Date of Patent: Aug. 25, 1992

[54] SYSTEM, DEVICE AND METHOD FOR SKIN CONTAMINATION DETECTION

[75] Inventor: Thomas D. Klingner, Prospect Heights, Ill.

[73] Assignee: Colormetric Laboratories, Inc., Des Plaines, Ill.

[21] Appl. No.: 747,268

[22] Filed: Aug. 19, 1991

[51] Int. Cl.$^5$ ............................................. A61B 5/00
[52] U.S. Cl. .................................. 128/636; 128/632
[58] Field of Search ..................... 128/632, 760-762, 128/771, 636-637; 604/289-290

[56] References Cited

U.S. PATENT DOCUMENTS

| | | |
|---|---|---|
| 2,890,797 | 6/1959 | Matthews . |
| 3,715,192 | 2/1973 | Wenz et al. . |
| 3,990,850 | 11/1976 | Friedman et al. ................. 128/636 |
| 4,329,999 | 5/1982 | Phillips .............................. 128/760 |
| 4,336,337 | 6/1982 | Wallis et al. . |
| 4,595,011 | 6/1986 | Phillips .............................. 128/771 |
| 4,658,833 | 4/1987 | Stuart ................................. 128/771 |
| 4,706,676 | 11/1987 | Peck . |
| 4,732,153 | 3/1988 | Phillips .............................. 128/771 |
| 4,819,645 | 4/1989 | Peck . |
| 4,821,733 | 4/1989 | Peck .................................. 128/760 |
| 4,846,182 | 7/1989 | Fogt et al. ......................... 128/632 |
| 4,957,108 | 9/1990 | Schoendorfer .................... 128/632 |
| 4,960,467 | 10/1990 | Peck . |

OTHER PUBLICATIONS

"Detection Limits of Chemical Spot Tests Toward Certain Carcinogens on Metal, Painted, and Concrete Surfaces", Weeks, Jr. et al., Analytic Chemistry, vol. 48, p. 2227 (1976).

"Percutaneous Absorption", 2nd Ed., pp. 335-342, Bronaugh & Maibach (1989).

"Environmetnal Sampling to Estimate Skin Exposure", Boeniger, NIOSH Manual of Analytical Methods, p. 65 et seq. (Sep. 7, 1990).

*Primary Examiner*—William E. Kamm
*Assistant Examiner*—J. R. Jastrzab
*Attorney, Agent, or Firm*—Emrich & Dithmar

[57] ABSTRACT

An absorbent collection strip has attached thereto a detection strip impregnated with a reagent to respectively form collection and detection regions of an integral pad. A dermal surface is wiped with the collection region to remove a contaminant of interest therefrom and collect it on the collection region, which is then wetted with a solvent which has a selective affinity for the contaminant. The solvent carries the contaminant or a reaction product thereof by capillary action through the collection region to the detection region where it reacts with the reagent to produce a color change which indicates the presence of the contaminant. The collection region may also be impregnated with a substance for either facilitating removal of the contaminant from the dermal surface or for cooperation with the reagent in producing the color reaction. The solvent may be either inert to the reagent or may cooperate with it in producing the color reaction. The detection region may be impregnated with plural reagents at physically spaced-apart locations, the reagents being combined by operation of the solvent to produce the color reaction.

19 Claims, 1 Drawing Sheet

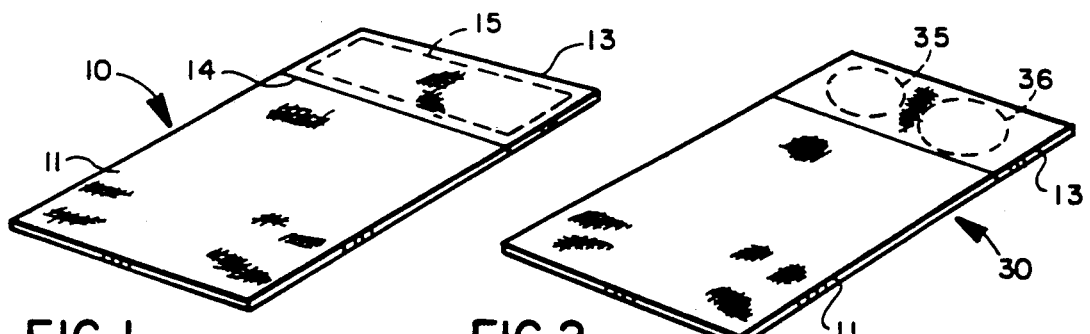
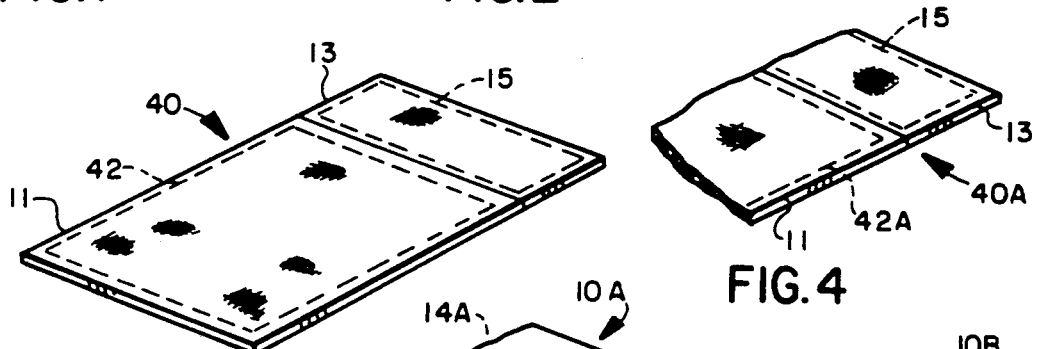
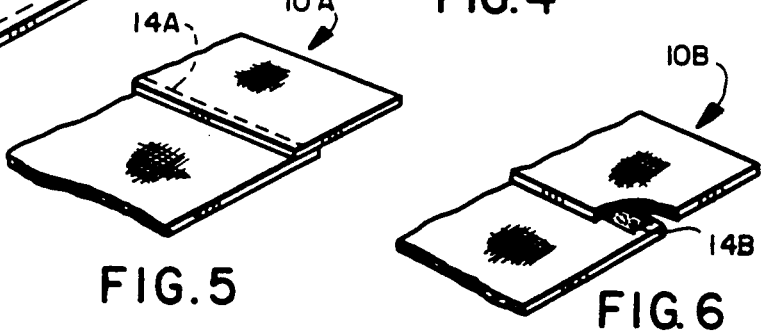
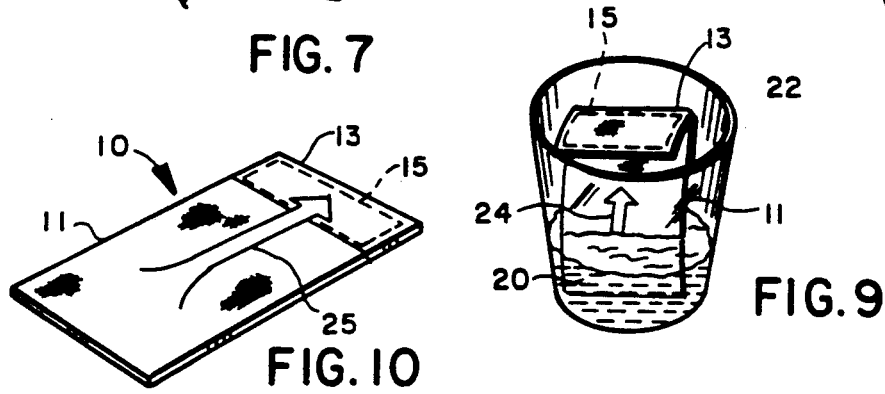

SYSTEM, DEVICE AND METHOD FOR SKIN CONTAMINATION DETECTION

BACKGROUND OF THE INVENTION

1. Field of the Invention

The present invention relates to techniques for assessing skin exposure to contaminants, such as toxic chemicals or the like.

2. Description of the Prior Art

Skin exposure constitutes an important route of entry into the human body for a large number of toxic chemicals. Circumstances may exist where absorption through the skin may equal or exceed the amount of chemical taken in through inhalation over a given period of time, such as an eighthour workday. Toxic contaminants may either affect the skin itself or have systemic toxicity, the extent of the effect depending upon the physical and chemical properties of the contaminant, the anatomical area of contact, the duration of contact and inter-personal variability, as well as environmental conditions. Various decontamination procedures have been adopted for certain workplace environments to remove contaminants from the skin, but it is first necessary to detect the presence of the contaminant on the skin to determine whether decontamination procedures are called for.

Methods previously used to assess skin exposure to toxic chemicals in the workplace include visual examination of the skin for discoloration or other visible effects, the use of an absorbent pad placed next to the skin to collect contaminants during the workday, and testing of the skin by wiping or washing it to remove and collect contaminant materials therefrom. Visible examination of the skin may not be effective in many cases where skin change does not occur until after a considerable length of time or after the cumulative effects of a number of periods of exposure. A major limitation of prior wiping and absorbent pad collection techniques is the requirement for laboratory analysis of the skin wipe or absorbent pad for contamination, which results in delayed reporting of results and increased costs.

Thus, for example, in U.S. Pat. No. 4,706,676, there is disclosed a dermal substance collection device for removing substances from the skin for later analysis. Similarly, in U.S. Pat. No. 2,890,797, there is disclosed a device having a circular region for absorbing a collected material and a contiguous peripheral region to which the collected material migrates for later testing by adding suitable solvents or the like to the peripheral region.

It is also known to provide indicator devices for immediate on-site indication of the presence of a substance. Thus, for example, U.S. Pat. No. 3,715,192 discloses an indicator strip which has a capillary material impregnated with the reagents and is confined between impermeable layers, being open only along its peripheral edges for directly absorbing a liquid medium to be examined for reaction with the impregnated reagents to give a color change or other indication of the presence in the liquid of the contaminant of interest. But this device is useful only with contaminants which are already in liquid media which can be easily absorbed up through the very small exposed surface area at the edge of the indicator strip. Furthermore, dirt or other foreign material in the liquid medium being tested may interfere with detection of the contaminant of interest.

SUMMARY OF THE INVENTION

It is a general object of the present invention to provide an improved technique for skin contamination detection, which avoids the disadvantages of prior techniques while affording additional structural and operating advantages.

An important feature of the invention is the provision of a method for effectively removing a contaminant from the skin and providing an immediate indication of its presence.

In connection with the foregoing feature, another feature of the invention is the provision of a method of the type set forth which effectively filters out the effects of dirt or other foreign material on the skin which may interfere with the ability to detect the contaminant of interest.

Another feature of the invention is the provision of a method of the type set forth which is extremely simple and cost-effective.

In connection with the foregoing features, it is another feature of the invention to provide a system for performing the method of the type set forth.

In connection with the foregoing features, a further feature of the invention is the provision of a method and system of the type set forth which enhances the sensitivity of the detection by concentrating the contaminant.

Yet another feature of the invention is the provision of a device usable in the system and method of the present invention for collecting a contaminant from a dermal surface and for testing in situ for the presence of the contaminant.

Certain of these and other features of the invention are attained by providing a device for the collection of a contaminant from a dermal surface and detection of the contaminant, comprising: a pad, the pad having a collection region of absorbent material for removing the contaminant from the dermal surface, the pad having a detection region integral with the collection region so as to permit transfer by capillary action from the collection region to the detection region of an associated solvent containing the collected contaminant or a product thereof; and reagent means carried by the detection region and responsive to contact with transferred contaminant or a product thereof to produce an indication of the presence of the contaminant.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there are illustrated in the accompanying drawings preferred embodiments thereof, from an inspection of which, when considered in connection with the following description, the invention, its construction and operation, and many of its advantages should be readily understood and appreciated.

FIG. 1 is a perspective view of a pad constructed in accordance with a first embodiment of the present invention;

FIG. 2 is a view similar to FIG. 1, illustrating a pad in accordance with a second embodiment of the invention;

FIG. 3 is a view similar to FIG. 1, illustrating a pad in accordance with a third embodiment of the invention;

FIG. 4 is a fragmentary, perspective view of a pad in accordance with a fourth embodiment of the invention;

FIG. 5 is a fragmentary, perspective view of a pad in accordance with a fifth embodiment of the invention;

FIG. 6 is a view similar to FIG. 5, illustrating a pad in accordance with a sixth embodiment of the invention;

FIG. 7 is a perspective view illustrating the use of the pad of FIG 1 in a first step of a method in accordance with the present invention;

FIG. 8 is a perspective view illustrating the use of the pad of FIG. 1 in accordance with a second step of the method of this invention;

FIG. 9 is a perspective view illustrating the use of the pad of FIG. in a third step of a method of this invention; and FIG. 10 is a perspective view illustrating the use of a strip of FIG. 1 in a fourth step of the method of this invention.

DESCRIPTION OF THE PREFERRED EMBODIMENTS

FIG. 1 illustrates a collection and detection pad 10, constructed in accordance with a first embodiment of the present invention. The pad 10 is generally rectangular in shape and includes a relatively large rectangular collection region 11 at one end thereof and a rectangular detection region 13 at the other end thereof joined together at a junction 14. While the pad 10 and each of the collection and detection regions and 13 have been illustrated as rectangular in shape, it will be appreciated that any other desired shapes could be used.

Each of the collection region and the detection region 13 is formed of an absorbent material, which may be in the form of a woven fabric and may be composed of cellulose or synthetic material, such as polypropylene or the like. Preferably the collection region and the detection region 13 are formed of the same material, but they may be formed of different materials. Each is fabricated so as to facilitate a wicking action whereby a liquid material may pass by capillary action from one end of the pad 10 to the other. Preferably, the collection and detection regions and 13 are, respectively, formed of separate strips of material which are joined together along a junction 14 to form an integral pad 10. The junction 14 may be formed by a heat bonding process, particularly if the two strips are formed of the same material. Referring to FIGS. 5 and 6, there are illustrated alternative pads respectively designated 10A and 10B in which the collection and detection strips are overlapped. In the pad 10A, the strips are joined at a junction 14A formed by stitching, and in the pad 10B, the strips are joined at a junction 14B formed by an adhesive material. The junctions 14A and 14B are particularly useful where the two strips are formed of different materials or where a heat bonding process would be otherwise inappropriate.

The detection region 13 of the pad 10 is impregnated with a detection reagent 15 over an area indicated by the broken line in FIG. 1. The reagent 15 is selected to react with a contaminant of interest or a product thereof to produce a color change.

In use, the collection region 11 of the pad 10 is wiped over a dermal area 16, such as the hand 17 in FIG. 7, which may have been exposed to a contaminant of interest, thereby to remove the contaminant from the dermal area 16 and collect it on the collection region 11 of the pad 10. The collection region 11 carrying the collected material is then wetted with a suitable solvent 20, such as by immersing the collection region 11 in a container 22 of the solvent 20, to saturate the collection region 11, as illustrated in FIGS. 8 and 9. The solvent 20 wicks up along the collection region 11 in the direction of the arrow 24 in FIG. 9, and into the detection region 13, as indicated by the arrow 25 in FIG. 10. Preferably, the solvent 20 has a selective affinity for the contaminant of interest. Thus, as the solvent 20 is wicked by capillary action through the collection region 11, it removes the contaminant of interest from any other materials, such as dirt or other foreign material which may have been collected from the dermal area 16, and carries the contaminant of interest into the detection region 13. Thus, it will be appreciated that the action of the solvent 20 serves to filter out foreign materials and to concentrate the contaminant of interest in the detection region 13.

As the contaminant of interest is carried into the detection region 13 by the solvent 20, it reacts with the reagent 15 to produce a color indication which signifies the presence of the contaminant. The color change reaction may be quantitative and/or qualitative. Thus, it may indicate not only the presence of a particular contaminant, but may also indicate, by the intensity of the color change, the concentration of the contaminant of interest. In this regard, it will be appreciated that the sensitivity of the detection is enhanced by the concentration of the contamination of interest in the solvent 20.

Alternatively, the solvent 20 may be selected so as to react with the contaminant of interest to produce a reaction product, the solvent 20 then carrying the reaction product into the detection region 13, where the reaction product in turn reacts with the reagent 15 to produce the color change detection reaction.

Referring to FIG. 2, there is illustrated an alternative collection and detection pad 30, which is substantially the same as the pad 10, except that, instead of the detection region 13 being impregnated with a single reagent 15, it is impregnated with two different reagents 35 and 36 at two spaced-apart areas of the detection region 13, each illustrated in broken line. The pad 30 is used in the same manner as was described above in connection with the pad 10 of FIG. 1, except that in this case the color detection reaction necessitates the use of two reagents 35 and 36 which are incompatible, so that they must be stored in separated impregnated areas of the detection region 13. In this case the solvent 20, in addition to carrying the contaminant of interest to the detection region 13, also serves to bring the two reagents 35 and 36 together to permit the color change reaction to occur in response to the presence of the contaminant.

Referring to FIG. 3, there is illustrated an alternative collection and detection pad 40, which is substantially the same as the pad 10, except that in this case the collection region is also impregnated with a chemical substance 42 over substantially the entire area thereof, as indicated in broken line, the substance 42 being selected to facilitate removal of the contaminant of interest from the dermal area 16. The chemical substance 42 may be a suitable solvent which is non-toxic and compatible with the human skin and which is a good solvent for the contaminant of interest. Preferably, the chemical substance 42 will also have a relatively high molecular weight, preferably above 400, to prevent absorption through the skin.

Referring to FIG. 4, there is illustrated an alternative collection and detection pad 40A, which is substantially identical to the pad 40, except that the collection region is impregnated with a chemical substance 42A over substantially the entire area thereof, as indicated by the broken line, the chemical substance 42A being selected to participate in the color change reaction of the reagent 15 in the detection region 13. Thus, for example, the pad 40A may be used in the same manner as was described above in connection with the pad 10, except that the chemical substance 42A, either alone or in cooperation with the solvent 20, may react with the contaminant of interest to produce a reaction product which is then carried by the solvent 20 into the detection region 13, the reaction product of the contaminant in turn reacting with the reagent 15 to produce the color change reaction.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure.

EXAMPLE I

Test for Aromatic Amines

A loosely woven polypropylene cloth pad 40 has the collection region 11 thereof saturated with a 15% solution of a high molecular weight (600) polyethylene glycol in methanol. The methanol is evaporated, leaving a slightly greasy loading of glycol on the collection region 11 of the pad 40, which serves to facilitate removal of aromatic amines from human skin. The detection region 13 of the pad 40 is impregnated with a solution of 2.0 gm naphthol AS as a color coupling reagent, along with 1.5 gm potassium acetate as a buffer and 1.25 gm sodium nitrite in 300 ml. of methanol. The methanol is evaporated from the detection region 13 to leave a dry reagent system 15 on the pad 40.

In use, a dermal area 16 is wiped with the collection region 11 of the pad 40 to remove aromatic amines. The collection region 11 is then dipped into a container 22 containing a water solution of an acid pH surfactant in sufficient quantity to saturate the collection region 11. Any collected aromatic amine is dissolved in the water solution of acid pH water surfactant, and the solution is wicked up the pad 40 by capillary action and carries the dissolved aromatic amine to the detection region 13. The acid p of the solution activates the stable chemicals in the detection region 13, causing any aromatic amine present to diazotize and couple with the naphthol AS to create a color change. The amount of color formed is in proportion to the amount of aromatic amine contamination present.

In modifications of EXAMPLE I, the chemical substance 42 in the collection region 11 may be other types of high molecular weight cosmetic grade material, such as polypropylene glycol or ethoxylated derivatives. The reagent 15 may incorporate a wide range of coupling reagents other than naphthol AS. Also, other buffers or nitrite salts such as potassium nitrite could be used, or solvents such as acidic methanol or acetone. Alternatively, other reagent systems, such as aromatic aldehydes or fluorescent reagents may be used for the detection of aromatic amines.

EXAMPLE II

Test for Aromatic Isocyanates

The pad 40 is constructed as explained above for EXAMPLE I, except that the solvent 20 in the container 22 is hexane. The detection reagent 15 will react directly with collected aromatic isocyanates when they reach the detection region 13 to form a colored compound in proportion to the amount of isocyanate present. In this example, it will be appreciated that the solvent 20 is inert to the detection chemistry.

In modifications of EXAMPLE II, the solvent 20 may be another organic solvent such as toluene, that is an effective solvent for the isocyanate but does not contain an acid or other chemical group that will react with the isocyanate.

From the foregoing, it can be seen that there has been provided an improved system, method and device for effectively collecting and detecting a contaminant of interest in situ, without the need for laboratory analysis, while at the same time enhancing the sensitivity of the detection by filtering out foreign materials and concentrating the contaminant in the detection reaction.

I claim:

1. A device for the collection of a contaminant from a dermal surface and detection of the contaminant, comprising: a pad, said pad having a collection region of absorbent material for removing the contaminant from the dermal surface, said pad having a detection region integral with said collection region and disposed in non-overlapping and non-surrounding relationship therewith so as to permit transfer by capillary action from said collection region to said detection region of an associated solvent containing the contaminant or a product thereof, said collection region and said detection region being distinct elements attached to each other; and reagent means carried by said detection region and responsive to contact with transferred contaminant or a product thereof to product an indication of the presence of the contaminant.

2. The device of claim 1, wherein each of said collection region and said detection region is a substantially flat member having a peripheral edge, each of said regions being attached to the other along only a portion of the peripheral edge thereof.

3. The device of claim 1, wherein said collection region and said detection region are formed of the same material.

4. The device of claim 1, wherein said detection region is impregnated with said reagent means.

5. The device of claim 1, wherein said reagent means includes plural reagents respectively disposed at spacedapart areas of said detection region.

6. The device of claim 1, wherein said collection region carries a chemical substance.

7. The device of claim 6, wherein said chemical substance includes a composition to facilitate removal of the contaminant from the dermal surface.

8. The device of claim 6, wherein said chemical substance includes a composition to cooperate with said reagent means in detecting the presence of the contaminant.

9. The device of claim 1, wherein said reagent means includes means reactable with a transferred contaminant or a product thereof to effect a color change in said detection region.

10. A system for collecting a contaminant from a dermal surface and detecting the contaminant, comprising: a collection pad of absorbent material for removing the contaminant from the dermal surface, a detection pad integral with said collection pad so as to permit transfer of liquid by capillary action from said collection pad to said detection pad, a liquid solvent having a selective affinity for the contaminant such that when said collection pad is wetted thereby said solvent will cooperate with said collection pad to transfer the contaminant or a product thereof by capillary action to said detection pad, and reagent means carried by said detection pad and responsive to contact with a transferred contaminant or a product thereof to product an indication of the presence of the contaminant.

11. The system of claim 10, wherein said solvent is inert to said reagent means.

12. The system of claim 10, wherein said solvent includes a substance which cooperates with said reagent means in detecting the presence of the contaminant.

13. The system of claim 12, wherein said substance includes a composition which reacts with the contaminant to produce a product which is in turn reactive with said reagent means.

14. The system of claim 10, wherein said reagent means includes a composition which is reactive with the contaminant itself to produce an indication of the presence of the contaminant.

15. A method for collecting a contaminant from a dermal surface and detecting the contaminant, comprising the steps of: providing a pad having an absorbent collection region and a detection region carrying a reagent chemically reactive with the contaminant or a product thereof to produce an indication of the presence of the contaminant, wiping the dermal surface with the collection region of the pad to remove the contaminant from the dermal surface and collect it on the collection region of the pad; wetting the contaminant-carrying collection region of the pad with a liquid solvent having a selective affinity for the contaminant so as to transfer the contaminant or a product thereof by capillary action from the collection region to the detection region; and observing the chemical reaction in the detection region between the reagent and the contaminant or a product thereof.

16. The method of claim 15, wherein said wetting step is effected by dipping the contaminant-carrying collection region of the pad into the liquid solvent.

17. The method of claim 15, and further comprising the step of producing a reaction between the contaminant and the solvent to produce a product which is in turn reactive with the reagent means.

18. The method of claim 15, wherein the observing step includes observing a color change in the detection region.

19. The method of claim 18, wherein the observing step includes observing the degree of color change to provide a quantitative indication of the amount of contaminant collected.

* * * * *

UNITED STATES PATENT AND TRADEMARK OFFICE
CERTIFICATE OF CORRECTION

PATENT NO. : 5,140,986
DATED      : August 25, 1992
INVENTOR(S) : Thomas D. Klingner It is certified that error appears in the above-identified patent and that said Letters Patent is hereby corrected as shown below:

Column 6, line 41, "product" second occurrence should be --produce--;

line 55, "spacedapart" should be --spaced apart--.

Column 7, line 14, "product" second occurrence should be --produce--.

Signed and Sealed this

Seventh Day of September, 1993

Attest:

BRUCE LEHMAN

*Attesting Officer*      *Commissioner of Patents and Trademarks*